United States Patent
Li et al.

(10) Patent No.: US 12,060,595 B2
(45) Date of Patent: Aug. 13, 2024

(54) METHOD FOR IMPROVING EFFICIENCY OF ANAEROBIC FERMENTATION IN MEDIUM TEMPERATURE-HIGH TEMPERATURE TRANSITION ZONE

(71) Applicant: WELLE ENVIRONMENTAL GROUP CO., LTD., Changzhou (CN)

(72) Inventors: Yuezhong Li, Changzhou (CN); Changda Cai, Changzhou (CN); Yabin Gong, Changzhou (CN); Ouru Zhan, Changzhou (CN); Qian Li, Changzhou (CN)

(73) Assignee: WELLE ENVIRONMENTAL GROUP CO., LTD., Changzhou (CN)

( * ) Notice: Subject to any disclaimer, the term of this patent is extended or adjusted under 35 U.S.C. 154(b) by 0 days.

(21) Appl. No.: 18/031,880

(22) PCT Filed: Sep. 28, 2021

(86) PCT No.: PCT/CN2021/121384
§ 371 (c)(1),
(2) Date: Apr. 14, 2023

(87) PCT Pub. No.: WO2022/078207
PCT Pub. Date: Apr. 21, 2022

(65) Prior Publication Data
US 2023/0392171 A1  Dec. 7, 2023

(30) Foreign Application Priority Data

Oct. 17, 2020  (CN) .......................... 202011113273.9

(51) Int. Cl.
| | | |
|---|---|---|
| C12P 5/02 | (2006.01) | |
| C12M 1/02 | (2006.01) | |
| C12M 1/06 | (2006.01) | |
| C12M 1/107 | (2006.01) | |

(52) U.S. Cl.
CPC ............. *C12P 5/023* (2013.01); *C12M 21/04* (2013.01); *C12M 27/02* (2013.01); *C12M 41/22* (2013.01)

(58) Field of Classification Search
CPC ........ C12P 5/023; C12M 21/04; C12M 27/02; C12M 41/22
See application file for complete search history.

(56) References Cited

FOREIGN PATENT DOCUMENTS

| | | |
|---|---|---|
| CN | 102583930 A | 7/2012 |
| CN | 105925361 A | 9/2016 |
| CN | 107511388 A | 12/2017 |
| CN | 111484219 A | 8/2020 |
| CN | 112280805 A | 1/2021 |

OTHER PUBLICATIONS

Bai Na, The Study on Biogas Fermentation and Dynamic Technology of Agriculture Organic Wastes, Chinese Academy of Agricultural Sciences Master Dissertation, 2011, pp. 1-77.
Nuruol Syuhadaa Mohd, et al., Anaerobic Digestion at 45° C for Sludge Treatment: A Trade-off between Performances and Capability in Producing Class a Biosolids, International Journal of Environmental Science and Development, 2016, pp. 399-405, vol. 7, No. 6.
Jiang Xinru, et al., Effect of leachate recirculation on sewage sludge anaerobic digestion, Chinese Journal of Applied and Environmental Biology, 2021, pp. 459-465, vol. 27, No. 2.
Li Yue-Zhong, et al., Experimental Study and Engineering Verification to Improve the Anaerobic Fermentation Efficiency of in Mesophilic and Thermophilic Temperature Intermediate Zone, China Biogas, 2021, pp. 51-56, vol. 39, No. 2.
Gong Yabin, et al., Anaerobic Biogas Production Efficiency of Food Waste at the Medium Temperature and Intermediate Temperature Zone, Environmental Engineering, 2022, pp. 132-138, vol. 40, No. 3.
Sebastian Hupfauf, et al., Temperature shapes the microbiota in anaerobic digestion and drives efficiency to a maximum at 45° C, Bioresource Technology, 2018, pp. 1-30.
Shin Chul, et al., Sewage sludge treatment, 1981, pp. 5-7, 58-61.
Hu Jicui, Theory and Technology of Anaerobic Biological Treatment of Wastewater, 2002, pp. 8-10, 121-127.
Tatsuya Noike, Theory and Technology of Anaerobic Biological Treatment of Wastewater, 2014.
GB/T51063-2014, Technical code for large and medium-scale biogas engineering, 2014, pp. 1-57.
HJ 2023-2012, Technical specifications of expanded granular sludge bed (EGSB) reactor for wastewater treatment, 2013, pp. 1-17.

*Primary Examiner* — Thane Underdahl
(74) *Attorney, Agent, or Firm* — Bayramoglu Law Offices LLC (57) ABSTRACT

A method for improving efficiency of anaerobic fermentation in a medium temperature-high temperature transition zone includes: After being subjected to heat exchange through a front heat exchanger, hydrolyzed slurry is pumped to a bottom of an anaerobic tank. A temperature of the slurry is controlled at 45±0.2° C. A central agitator is turned on after feeding is completed, to slowly gently stir the slurry in the anaerobic tank, and the central agitator is turned off after the slurry is uniformly mixed. In an operating state, making medium-temperature anaerobic flora and high-temperature anaerobic flora in methanogenic bacteria in the anaerobic sludge overlap at the fermentation temperature and be fully mixed with and in contact with the slurry, to continuously treat and convert organic substances in the slurry when the slurry is under an anaerobic fermentation condition in a medium temperature-high temperature transition zone.

5 Claims, 9 Drawing Sheets

METHOD FOR IMPROVING EFFICIENCY OF ANAEROBIC FERMENTATION IN MEDIUM TEMPERATURE-HIGH TEMPERATURE TRANSITION ZONE

CROSS REFERENCE TO THE RELATED APPLICATIONS

This application is the national phase entry of International Application No. PCT/CN2021/121384, filed on Sep. 28, 2021, which is based upon and claims priority to Chinese Patent Application No. 202011113273.9, filed on Oct. 17, 2020, the entire contents of which are incorporated herein by reference.

TECHNICAL FIELD

The present invention relates to a method for improving efficiency of anaerobic fermentation in a medium temperature-high temperature transition zone, and belongs to the technical field of anaerobic fermentation processes.

BACKGROUND

Anaerobic fermentation refers to a process in which waste is stabilized by metabolic activity of microorganisms under anaerobic conditions, accompanied by production of methane and $CO_2$, and is a treatment manner of decomposing most biodegradable organic substances in garbage and converting them into biogas. Therefore, the anaerobic fermentation process has been widely applied to treatment of wastewater and organic solid waste.

Figure 1:
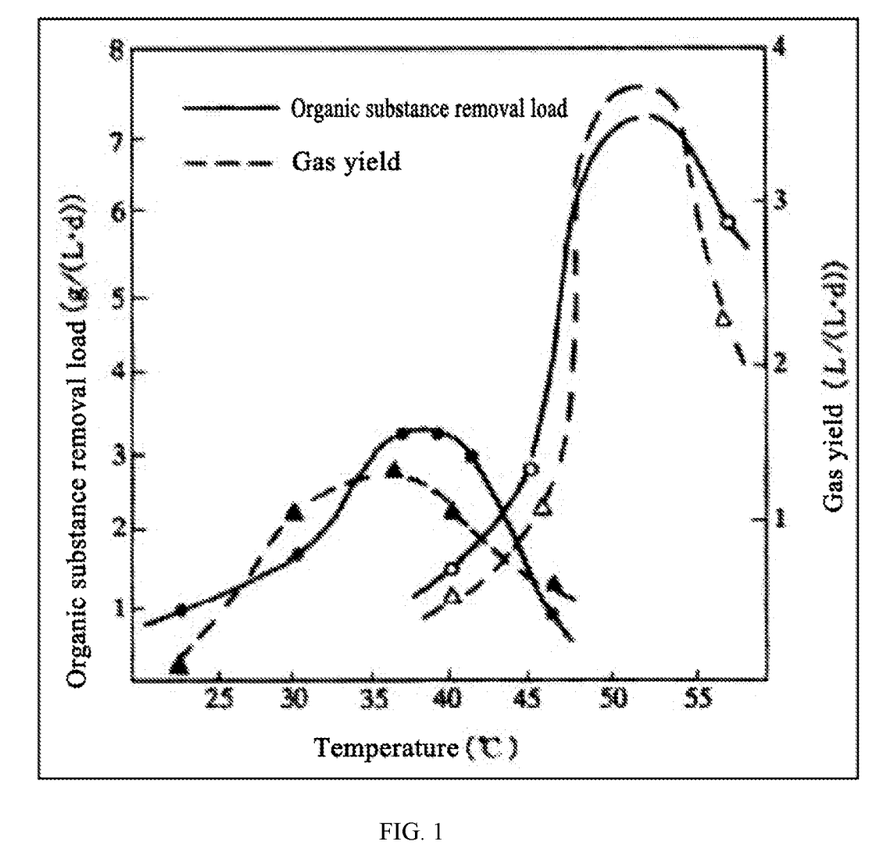
FIG. 1 is a curve graph between an organic substance removal load and a gas yield at temperatures of existing anaerobic fermentation.

The temperature in anaerobic fermentation is an important factor affecting the efficiency of anaerobic fermentation. According to different temperature ranges, anaerobic fermentation may be divided into normal temperature fermentation, medium-temperature fermentation, and high-temperature fermentation. However, the temperature of normal temperature fermentation varies due to fluctuations of the natural temperature in the environment. Because the efficiency and stability of anaerobic fermentation are poor, anaerobic fermentation is seldom used in engineering. Medium-temperature fermentation and high-temperature fermentation are usually used in engineering, the most suitable temperature range of medium-temperature fermentation is 35° C. to 40° C., and the most suitable temperature range of high-temperature fermentation is 50° C. to 55° C. A transition zone between medium-temperature fermentation and high-temperature fermentation is a valley in terms of an organic substance removal load and a yield rate, that is, the so-called low-speed anaerobic fermentation, as shown in FIG. 1, which is located between 40° C. and 45° C., and on both sides of which are a medium-temperature efficient zone and a high-temperature efficient zone. In 1968, the Japanese scholar Shin Okada first proposed this theory in the book "Sewage and Sludge Treatment". This theory was reiterated in the book "Theories and Technologies of Anaerobic Biological Treatment of Wastewater" compiled by Hu Jicui from Tsinghua University in 2002 and the book "Methane Fermentation" compiled by Japanese scholar Nochi Tatsuya in 2014. This theory is that: the suitable temperature for medium-temperature anaerobic fermentation ranges from 35° C. to 40° C., the suitable temperature for high temperature anaerobic fermentation ranges 50° C. to 55° C., and the medium temperature-high temperature transition zone of 40° C. to 45° C. is identified as a valley in terms of an organic substance removal load and a yield rate, that is, the so-called low-speed anaerobic fermentation zone. This theory has been written into the national standard GB/T51063-2014 Technical Code for Large and Medium-Scale Biogas Engineering and the national environmental protection standard (HJ2023-2012). For a long time, there has been a lack of in-depth study on the mechanism of anaerobic fermentation in the low-speed anaerobic zone, that is, the medium temperature-high temperature transition zone of 40° C. to 45° C., which is considered as a forbidden zone that cannot be used in engineering.

SUMMARY OF THE INVENTION

Technical Problem

An objective of the present invention is to provide a method for improving efficiency of anaerobic fermentation in a medium temperature-high temperature transition zone. A specific fermentation temperature in a specified medium temperature-high temperature transition zone can increase an operating load and an organic substance removal rate during treatment, significantly improve an impact-resistance load capacity and stability, improve anaerobic digestion efficiency and a gas yield rate, and reduce engineering construction costs and operating costs.

Technical Solution

A technical solution of the present invention for achieving the foregoing objective is: A method for improving efficiency of anaerobic fermentation in a medium temperature-high temperature transition zone includes the following steps:

(1) performing heat exchange on hydrolyzed slurry through a front heat exchanger, and then pumping the slurry into an anaerobic tank uniformly from a plurality of water distribution pipes at a bottom of the anaerobic tank, where a temperature of the slurry after the heat exchange performed through the front heat exchanger is 45±0.2° C., a thermal insulation layer and a warming device are arranged on a wall of the anaerobic tank, and an intermittently-operating central agitator with upper blades and lower blades is arranged inside the anaerobic tank;

(2) turning on, in an initial state, the central agitator after feeding is completed, to slowly gently stir the slurry in the anaerobic tank, and turning off the central agitator after uniformly mixing upper-layer, middle-layer, and lower-layer slurry in the anaerobic tank, where a concentration of anaerobic sludge in the anaerobic tank in the initial state is 5 to 15 g/l; and (3) controlling, in an operating state in which a pH value of the slurry in the anaerobic tank ranges from 6.8 to 7.8, and the concentration of the sludge in the anaerobic tank ranges from 20 to 30 g/l, the warming device, a biogas slurry reflux pump 3, and the central agitator on the anaerobic tank through an automatic control system, to control a fermentation temperature of the slurry at 44±1° C., making medium-temperature anaerobic flora and high-temperature anaerobic flora in methanogenic bacteria in the anaerobic sludge overlap at the fermentation temperature and be fully mixed with and in contact with the slurry, to continuously treat and convert organic substances in the slurry when the slurry is under an anaerobic fermentation condition in a medium temperature-high temperature transition zone.

Beneficial Effects

According to the present invention, during anaerobic digestion and treatment, a temperature of slurry entering into the anaerobic tank is precisely controlled, and the slurry in the anaerobic tank is subjected to anaerobic fermentation in a medium temperature-high temperature transition zone at 44±1° C., most of medium-temperature flora in methanogenic bacteria capable of using anaerobic sludge still continuously maintain anaerobic activity, and dominant bacteria of the medium-temperature anaerobic flora rapidly proliferate, while high-temperature flora also begin to proliferate and play a role, so that medium-temperature anaerobic flora of methanogenic bacteria overlap with high-temperature anaerobic flora of methanogenic bacteria, thereby enhancing the anaerobic activity. Under specified process conditions, multiple strains and slurry can be fully mixed and fermented, so that methanogenic bacteria can be subjected to anaerobic digestion and treatment under the best environmental conditions, thereby significantly improving the efficiency of anaerobic fermentation in the transition zone. Because the alkalinity during anaerobic treatment increases, which can effectively reduce impact of organic acid accumulation, anaerobic treatment has good buffering performance, and can ensure the stable operation of the anaerobic fermentation process. Compared with middle-temperature fermentation and high-temperature fermentation, the present invention has a higher operating load rate and a higher organic substance removal rate, significantly improves an impact-resistance load capacity and stability of an anaerobic reactor, improves anaerobic digestion efficiency and a gas yield rate of a device, and reduce engineering construction costs and operating costs.

BRIEF DESCRIPTION OF THE DRAWINGS

Embodiments of the present invention are further described below with reference to the accompanying drawings.

1—front heat exchanger, 2—anaerobic tank, 3—biogas slurry reflux pump, 4—biogas slurry reflux pipe, 5—central agitator, 6—water distribution pipe, 7—sludge-water separator, 8—temperature sensor, 9—sludge reflux pump, 10—hydrolysis tank, 11—silage pit.

DETAILED DESCRIPTION OF THE EMBODIMENTS

Figure 3:
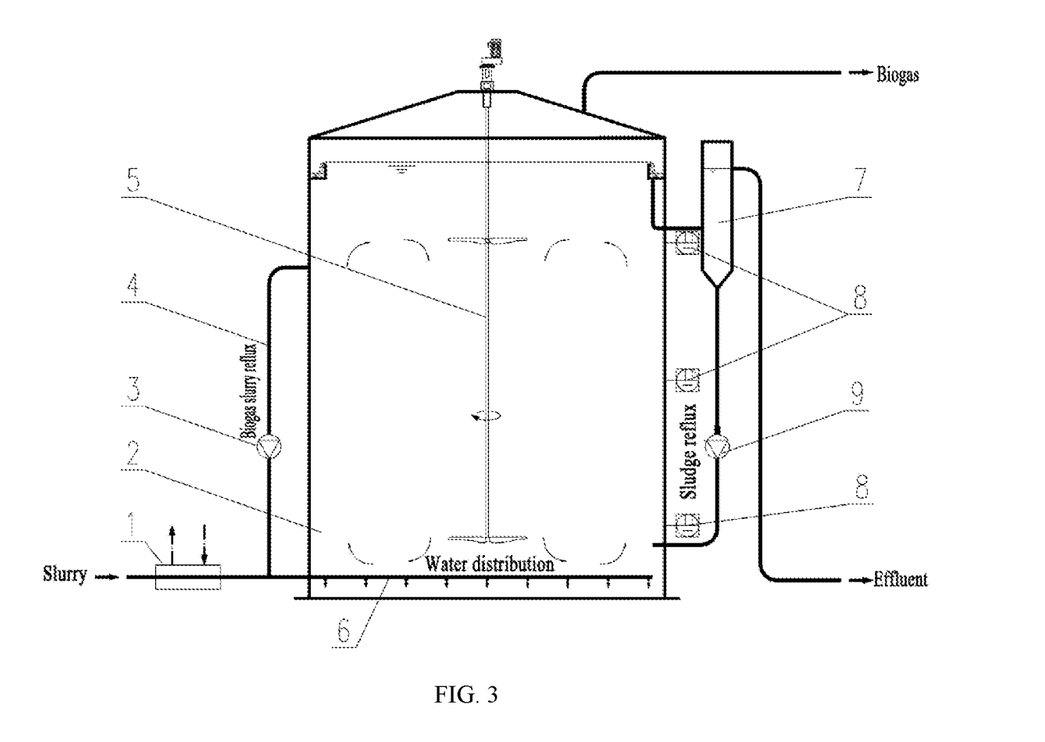
FIG. 3 is a schematic diagram of a process of performing anaerobic fermentation on food waste slurry and vinasse slurry according to the present invention.
Figure 6:
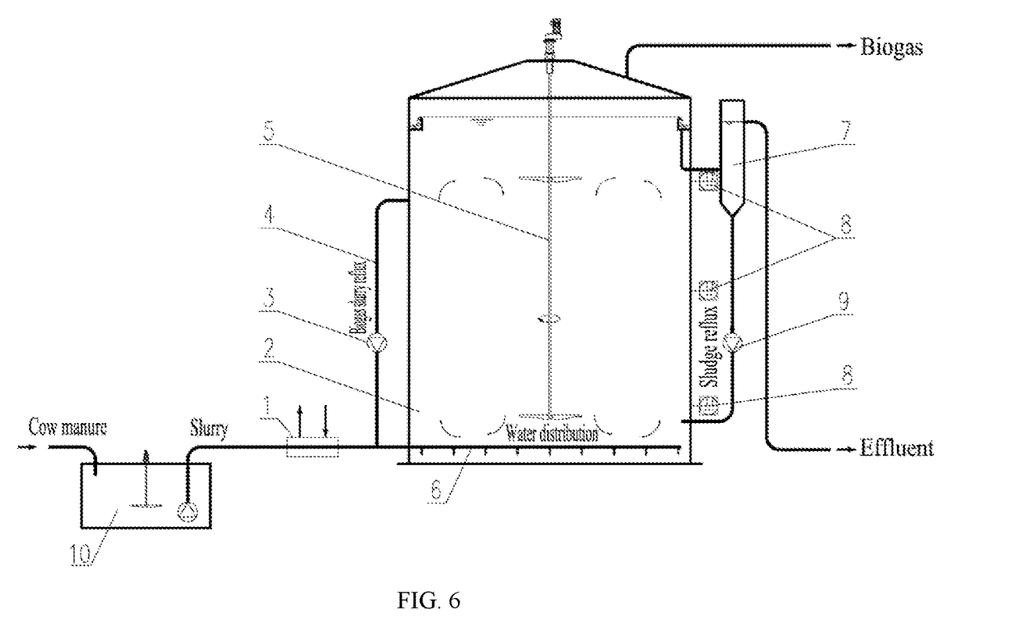
FIG. 6 is a schematic diagram of a process of performing anaerobic fermentation on cow manure slurry according to the present invention.
Figure 8:
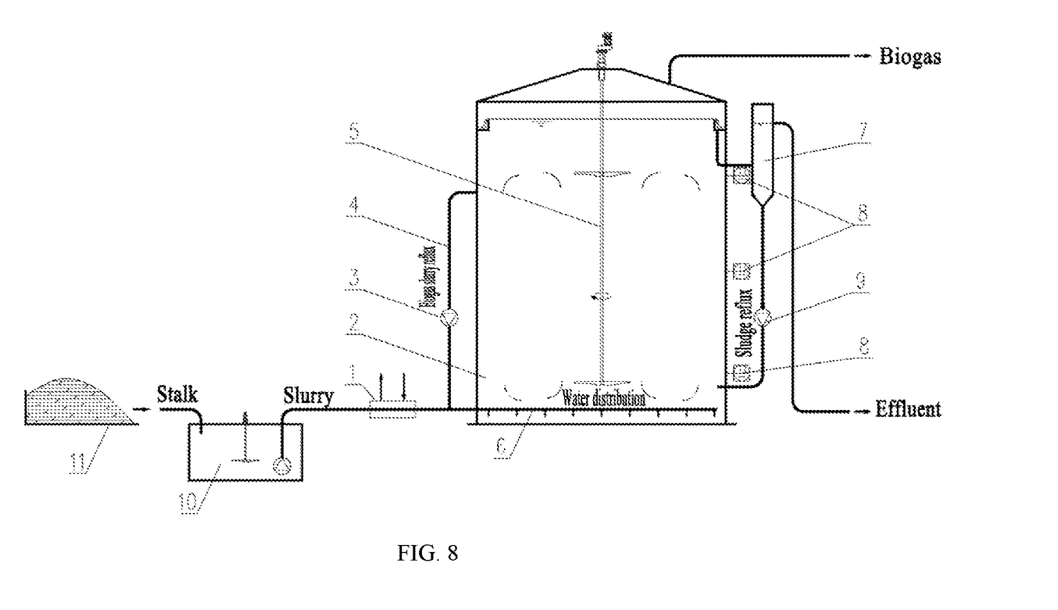
FIG. 8 is a schematic diagram of a process of performing anaerobic fermentation on stalk slurry according to the present invention.

The present invention provides a method for improving efficiency of anaerobic fermentation in a medium temperature-high temperature transition zone, including the following steps:

(1) Perform heat exchange on hydrolyzed slurry through a front heat exchanger 1, as shown in FIG. 3, FIG. 6, and FIG. 8, and then pump the slurry into an anaerobic tank 2 uniformly from a plurality of water distribution pipes 6 at a bottom of the anaerobic tank 2. The plurality of water distribution pipe 6 are symmetrically arranged at the bottom of a cylinder. For example, the anaerobic tank 2 is circular. The water distribution pipe 6 may be arranged in a staggered manner as a plurality of non-concentric circles. Water outlets on each water distribution pipe 6 are arranged from inside to outside along a circumferential direction. The coverage areas of the outlet holes are increased, to improve the uniformity of water distribution om the anaerobic reactor, and enhance the full mixing and contact between inlet water and anaerobic sludge. A temperature of the slurry after the heat exchange performed through the front heat exchanger 1 is 45±0.2° C., and the slurry entering into the tank is warmed or cooled, to control the temperature of the slurry during anaerobic treatment more accurately.

As shown in FIG. 3, FIG. 6, and FIG. 8, in the present invention, a thermal insulation layer and a warming device are arranged on a wall of the anaerobic tank 2, and an intermittently-operating central agitator with upper blades and lower blades is arranged inside the anaerobic tank. The thermal insulation layer is arranged on an outer side of the wall of the anaerobic tank 2, and the warming device may be a warming pipe, for example, using electric heating or heat after heat exchange in a processing system. A heat loss caused by an environmental temperature difference is compensated for and reduced through the warming device and the thermal insulation layer, to maintain a specified fermentation temperature during anaerobic treatment. In the present invention, the central agitator 5 may be an existing agitator, is arranged at a central position of the anaerobic tank 2, and is turned on after feeding completes. The central agitator 5 is turned on, and is turn off after the slurry is uniformly mixed, to keep the slurry entering into the anaerobic tank 2 in full contact with strains. As shown in FIG. 3, FIG. 6, and FIG. 8, in the present invention, a biogas slurry reflux pipe 4, a sludge-water separator 7, and a sludge reflux pump 9 are arranged on an outer side of the anaerobic tank 2. A plurality of temperature sensors 8 are installed on the wall of the anaerobic tank 1 and inside the anaerobic tank 1. A biogas slurry reflux pump 3 is arranged on the biogas slurry reflux pipe 4, to control a pH value of the slurry and maintain balance of methanogenic bacteria in the tank. When the biogas slurry reflux pump 3 needs to be turned on, the central agitator 5 may be turned on at the same time, and the warming device, the central agitator 5, and the biogas slurry reflux pump 3 are controlled by an automatic control system to work.

(2) Turn on, in an initial state, the central agitator 5 after feeding is completed, to slowly gently stir the slurry in the anaerobic tank 2, and turn off the central agitator 5 after uniformly mixing upper-layer, middle-layer, and lower-layer slurry in the anaerobic tank 2. The central agitator 5 may be turned off after stirring for about 2 hours. A rotational speed of the central agitator 5 is 12 to 15 r/min. A concentration of anaerobic sludge in the anaerobic tank 2 in the initial state is 5 to 15 g/l, which may be adjusted according to characteristics of different materials. For anaerobic sludge of food waste and vinasse, the concentration is 10 to 14.5 g/l, and for anaerobic sludge of cow manure, stalks, and the like, the concentration is 6 to 12 g/l. The anaerobic sludge is an existing active sludge after acclimation. For example, during first inoculation, an inoculation amount may be 65% to 75% of slurry and 25% to 35% of strains.

(3) In an operating state, a pH value of the slurry in the anaerobic tank 2 ranges from 6.8 to 7.8, where the pH value of the slurry may be controlled through biogas slurry reflux, and the concentration of the sludge in the anaerobic tank 2 ranges from 20 to 30 g/l, to maintain anaerobic fermentation in the best state. In the present invention, the warming device, the biogas slurry reflux pump 3, and the central agitator 5 on the anaerobic tank 2 are controlled through an automatic control system, to control a fermentation temperature of the slurry at 44±1° C. Medium-temperature anaerobic flora and high-temperature anaerobic flora in methanogenic bacteria in the anaerobic sludge are caused to overlap at the fermentation temperature and be fully mixed with and in contact with the slurry, to treat and convert organic substances in the slurry when the slurry is under an anaerobic fermentation condition in a medium temperature-high temperature transition zone, to make the organic substances become methane, carbon dioxide, and water. The gas is collected through an exhaust pipe, the discharge overflows from the anaerobic tank 2 to the sludge-water separator 7, and after sludge-water separation, the sludge reflux pump 9 refluxes the sludge to the bottom of the anaerobic tank 2, and the effluent separated by the sludge-water separator 7 is collected and discharged after being treated to meet standards.

Figure 2:
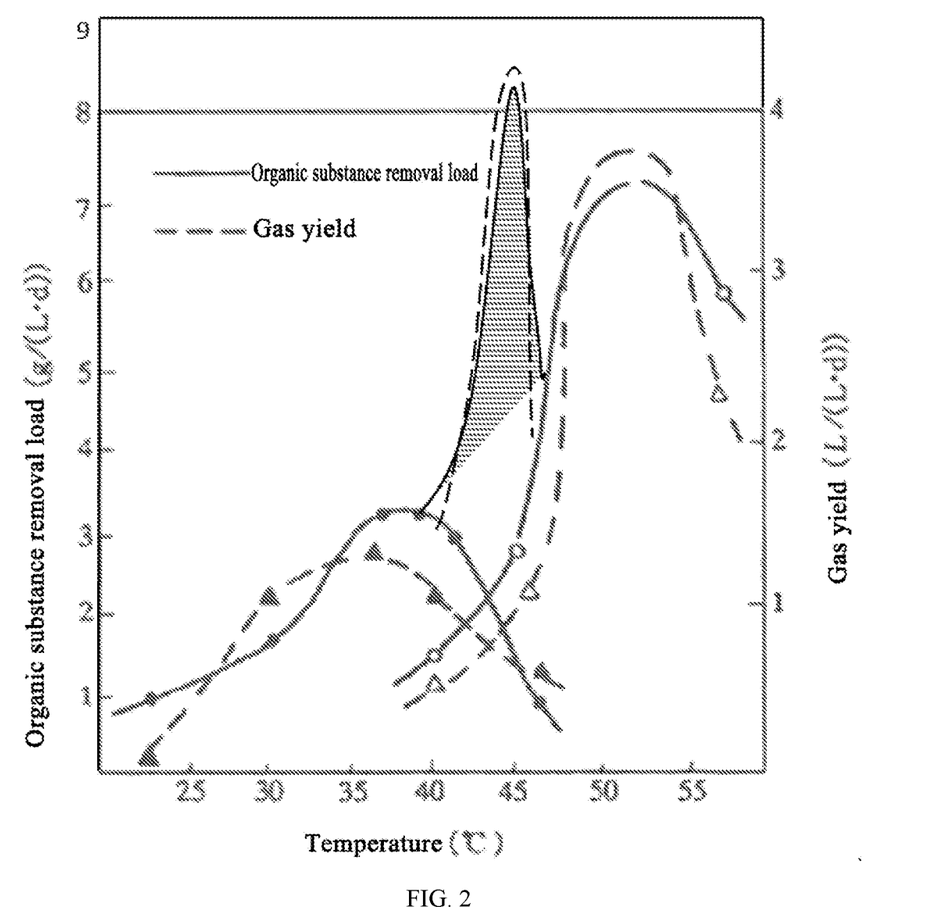
FIG. 2 is a curve graph between an organic substance removal load and a gas yield in a medium temperature-high temperature transition zone and at middle-temperature and high-temperature anaerobic fermentation temperatures according to the present invention.

In the present invention, the methanogenic medium-temperature anaerobic flora in anaerobic sludge include Methanobacillus formate, Methaniella zoe, Methanobacillus elvesii, Brachyceus rumenis, Methanobacillus bruceti, Methanobacillus vinnefii, Helicobacter heinne, Ococcus pasteurii, Methanobacillus mereson, Methanobacillus subground, Methanobacillus swamp, rumen polyethylene, Methanophilus, and Methanophila. Moreover, the high-temperature anaerobic flora include Methanobacillus thermophilus, Methanobacillus thermoforme, Methanobacillus Vornie, Methanobacillus thermoautotroph, Methanobacillus thermopoly. Because all of these anaerobic bacteria, for example, Methanobacillus formate, Methaniella zoe, Methanobacillus elvesii, Methanophilus, and Methanophila in medium-temperature anaerobic bacteria, can rapidly grow under a fermentation condition of 44±1° C., advantages of medium-temperature anaerobic flora are fully revealed. In addition, in the transition zone, high-temperature anaerobic bacteria also start to reproduce and function. Medium-temperature anaerobic flora and high-temperature anaerobic flora overlap in this transition zone, so that a best coordination effect can be produced, and fermentation efficiency can be significantly improved. FIG. 2 shows a curve graph between an organic substance removal load and a gas yield of food waste in a medium temperature-high temperature transition zone, a middle-temperature zone, and a high-temperature zone according to the present invention. It can be seen from FIG. 2 that the organic substance removal load in the medium temperature-high temperature transition zone is up to 8 g/(Ld), and the gas yield is up to 4 L/(Ld). Compared with those at a medium-temperature anaerobic suitable temperature of 35° C. to 40° C. and a high-temperature anaerobic suitable temperature of 50° C. to 55° C., the organic substance removal load and the gas yield are significantly increased.

In the present invention, to keep the fermentation temperature stable and reliable during operation, temperature sensors 8 for monitoring temperatures of layers of slurry and performing multi-point temperature measurement are arranged on the anaerobic tank 2. A plurality of measurement points are respectively arranged at the upper layer, the middle layer, and the lower layer, so that the temperature sensors 8 can monitor slurry temperature at different positions of respectively layers in time. When it is detected that a temperature difference between any two measurement points at a same layer is greater than 2° C. or a temperature difference between any two layers is greater than 2° C., the automatic control system automatically turns on the warming device, the central agitator 5, and the biogas slurry reflux pump 3. The automatic control system may be an existing control system, and heat the upper-layer, middle-layer, and lower-layer slurry through the warming device. The biogas slurry reflux pump 3 refluxes upper-layer biogas slurry to a lower layer. A reflux ratio of the biogas slurry to the slurry ranges from 2:1 to 6:1. For example, a reflux ratio of the biogas slurry to the slurry ranges from 3.1 to 5:1 or the like. The central agitator 5 slowly gently stirs the slurry, to ensure that the fermentation temperature in the anaerobic tank 2 is stabilized at the anaerobic fermentation temperature of 44±1° C., and make the slurry come into full contact with strains. When it is detected that a temperature difference between any two measurement points at a same layer is less than 1° C. or a temperature difference between any two layers is less than 1° C., the automatic control system automatically controls the warming device and the biogas slurry reflux pump 3 to stop working and the central agitator 5 lag to stop working, to implement stable operation of the devices, to enable the anaerobic reactor to achieve a higher operating load, a higher organic substance removal rate, and a capacity gas yield rate.

Example 1

As shown in FIG. 3, the slurry of the present invention was food waste slurry obtained after oil extraction and hydrolysis. Because before the food waste slurry entered the anaerobic tank 2, the food waste slurry was subjected to high-temperature oil extraction, and the temperature of the food waste slurry was about 70° C., the food waste slurry needed to be subjected to heat exchange through the front heat exchanger 1 before entering into the anaerobic tank 2, to be cooled to 45±0.2° C. A carbon-nitrogen ratio of the food waste slurry ranged from 13:1 to 15:1, and a TS concentration ranged from 10% to 20% by mass percentage. When a carbon-nitrogen ratio of the food waste slurry was 14:1, a TS concentration ranged from 12% to 18%, and a COD of the food waste slurry entering into the tank was lower than 30000 mg/l.

In an initial state, the central agitator 5 was turned on after feeding was completed, to slowly gently stir the slurry in the anaerobic tank 2 at 13±0.5 r/min, and the central agitator 5 was turned off after uniformly mixing upper-layer, middle-layer, and lower-layer slurry in the anaerobic tank 2, to make the slurry come into full contact with the anaerobic sludge. The stirring time may be 2±0.1 h. A concentration of anaerobic sludge in the anaerobic tank 2 in the initial state was 10 to 14 g/l.

Figure 4:
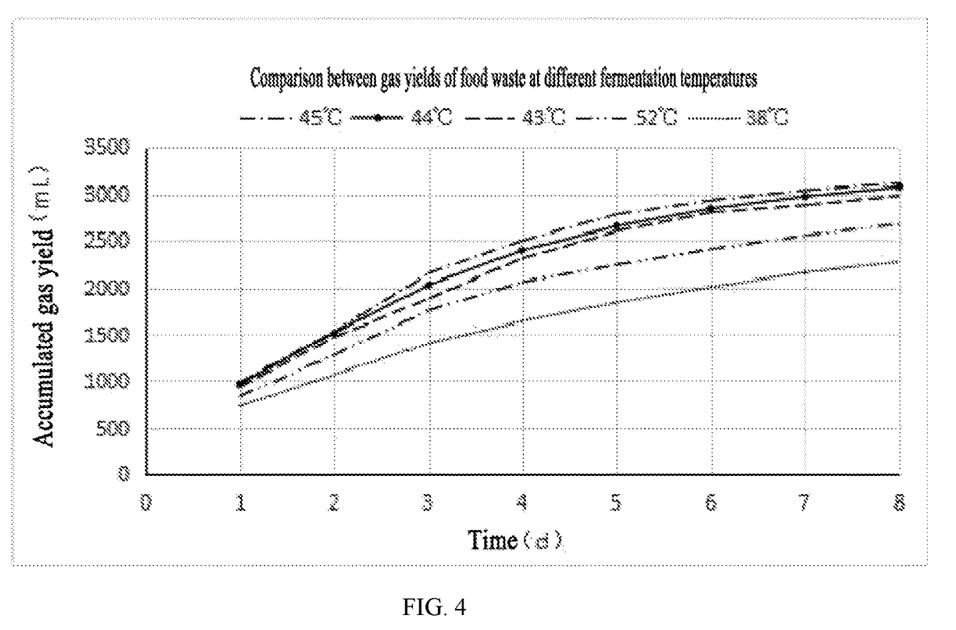
FIG. 4 is a schematic curve graph of comparison between gas yields of food waste at different fermentation temperatures according to the present invention.

During operation, the pH value of the slurry in the anaerobic tank 2 ranged from 7 to 7.5, the concentration of the sludge ranged from 24 to 28 g/l, the TS concentration of the slurry ranged from 3% to 4%, and the fermentation temperature of the slurry was controlled at 43° C., 44° C., and 45° C. respectively for anaerobic reaction. When the COD of the food waste slurry material ranged from 120000 to 180000 mg/i, the automatic control system automatically turned on the central agitator 5 and the biogas slurry reflux pump 3, refluxed upper-layer biogas slurry through the biogas slurry reflux pipe 4 and the water distribution pipe 6 to the lower layer of the anaerobic tank 2 by using the biogas slurry reflux pump 3. A reflux ratio of the biogas slurry to the food waste slurry ranged from 3.5:1 to 5.5:1, to dilute the slurry and make the COD of the food waste slurry entering into the tank lower than 30000 mg/l. After the feeding was completed, the biogas slurry reflux pump 3 was turned off, and the central agitator 5 lagged to be turned off. The central agitator 5 may be turned off 1 h later. FIG. 4 showed comparison between gas yields at different corresponding temperatures according to the present invention, where the fermentation temperatures of the slurry were 38° C., 43° C., 44° C., 45° C., and 52° C.

After the fermentation temperature of the slurry in the anaerobic tank 2 increased due to environmental factors, when it was detected that a temperature difference between any two measurement points at a same layer was greater than 2° C. or a temperature difference between any two layers was greater than 2° C., the automatic control system automatically turned on the warming device, the central agitator 5, and the biogas slurry reflux pump 3. The central agitator 5 slowly and gently stirred at 13 to 14 r/min. The biogas slurry reflux pump 3 refluxed biogas slurry and fresh food waste slurry according to a ratio of 3.5:1 to 5.5:1, to make the fresh material come into full and uniform contact with the anaerobic sludge. When it was detected that a temperature difference between any two measurement points at a same layer was less than 1° C. or a temperature difference between any two layers was less than 1° C., the automatic control system controls the warming device and the biogas slurry reflux pump 3 to stop working and the central agitator 5 lag to stop working. The temperature in the tank was controlled within a specified range, and organic substances in the food waste slurry were continuously treated and converted into methane, carbon dioxide, and water. The biogas was collected through an exhaust pipe. The effluent after sludge-water separation was collected for post-treatment, and discharged or partially reused after meeting standards.

It can be seen from FIG. 4 that in the present invention, the fermentation temperature of the food waste was controlled at 43° C., 44° C., and 45° C. Upon comparison between gas yields at 43° C., 44° C., and 45° C. and gas yields in the medium-temperature zone and the high-temperature zone, the gas yield efficiency at 44° C. in the transition zone was higher than the gas yield efficiency at 38° C. in the medium-temperature zone by 35.1% and was higher than the gas yield efficiency at 52° C. in the high-temperature zone by 14.9%. Moreover, the gas yield efficiency of the food waste at 43° C. and 45° C. in the transition zone was also higher than the gas yield efficiency at 38° C. in the medium-temperature zone and the gas yield efficiency at 52° C. in the high-temperature zone. The capacity load at a fermentation temperature in the transition zone may reach 7.5 KgCOD/m$^3$ d, the COD removal rate may reach 85% or above, and a capacity gas yield may reach 4 m$^3$/m$^3$ d so that the fermentation efficiency can be improved.

Example 2

The slurry of the present invention was hydrolyzed vinasse slurry. Because vinasse was brewing waste mash distilled at a high temperature of 90° C., as shown in FIG. 3, the vinasse was subjected to heat exchange through the front heat exchanger 1 before entering into the anaerobic tank 2, to be cooled to 45±0.2° C. A carbon-nitrogen ratio of the food waste slurry ranged from 13:1 to 15:1, and a TS concentration ranged from 6% to 8% by mass percentage. A COD of the vinasse entering into the tank was lower than 30000 mg/l. In an initial state, the central agitator 5 was turned on after feeding was completed, to slowly gently stir the slurry in the anaerobic tank 2 at 13 r/min to 14 r/min, and the central agitator 5 may be turned off after the stirring time reached 2±0.1 h, to uniformly mix upper-layer, middle-layer, and lower-layer slurry in the anaerobic tank 2, to make the slurry come into full contact with the anaerobic sludge. In addition, a concentration of anaerobic sludge in the anaerobic tank 2 in the initial state was 10 to 15 g/l.

During operation, the pH value of the slurry in the anaerobic tank 2 ranged from 7.2 to 7.6, the concentration of the sludge ranged from 25 to 30 g/l, the TS concentration of the slurry ranged from 3% to 4%, and the fermentation temperature of the slurry was controlled at 43° C., 44° C., and 45° C. respectively for anaerobic reaction. When the COD of the vinasse slurry material ranged from 60000 to 180000 mg/l, the automatic control system automatically turned on the central agitator 5 and the biogas slurry reflux pump 3. The central agitator 5 stirred at 13 r/min to 14 r/min. The biogas slurry reflux pump 3 refluxed upper-layer biogas slurry to the lower layer of the anaerobic tank 2. A reflux ratio of the biogas slurry to the food waste slurry ranged from 2.0:1 to 3.0:1. The reflux ratio of 2.5:1 may be used, to dilute the slurry and make the COD of the slurry entering into the tank lower than 30000 mg/l. After the feeding was completed, the biogas slurry reflux pump 3 was turned off. The central agitator 5 was turned off 1 h later. For specific temperature control, reference may be made to Example 1, but the reflux ratios were different. Organic substances in the food waste slurry were continuously treated and converted into methane, carbon dioxide, and water at specified fermentation temperatures. The biogas was collected through an exhaust pipe. The effluent after sludge-water separation was collected for post-treatment, and discharged or partially reused after meeting standards.

Figure 5:
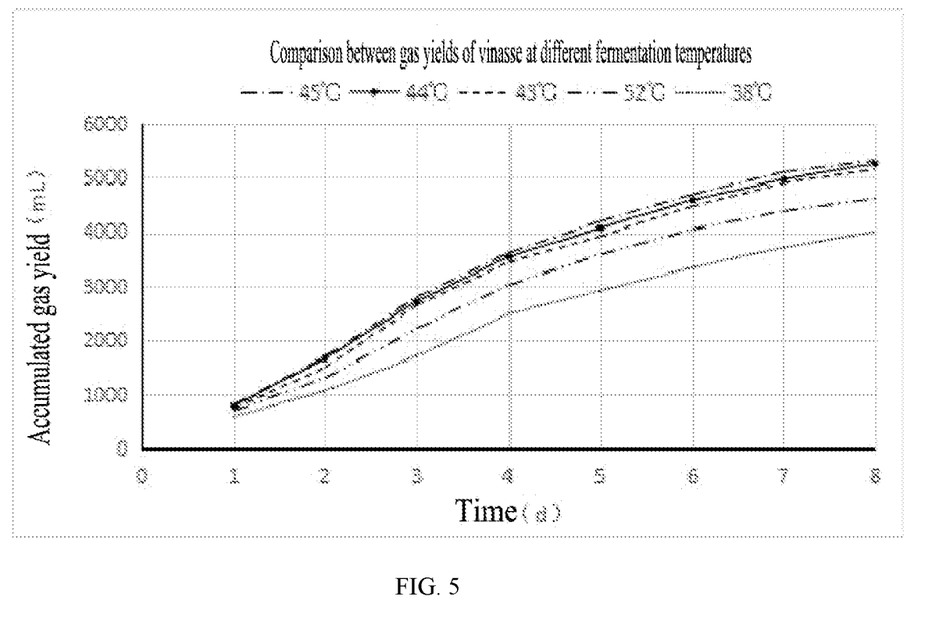
FIG. 5 is a schematic curve graph of comparison between gas yields of vinasse slurry at different fermentation temperatures according to the present invention.

FIG. 5 showed comparison between gas yields at different corresponding temperatures according to the present invention, where the fermentation temperatures of the slurry were 38° C., 43° C., 44° C., 45° C., and 52° C. It can be seen from FIG. 5 that in the present invention, the fermentation temperature of the vinasse slurry was controlled at 43° C., 44° C., and 45° C. Upon comparison between gas yields at 43° C., 44° C., and 45° C. and gas yields at 38° C. in in the medium-temperature zone and 52° C. in the high-temperature zone, the gas yield efficiency of the vinasse at 44° C. in the transition zone was higher than the gas yield efficiency at 38° C. in the medium-temperature zone by 30.6% and was higher than the gas yield efficiency at 52° C. in the high-temperature zone by 11.9%. The gas yield efficiency at 43° C. and 45° C. in the transition zone was also higher than the gas yield efficiency at 38° C. in the medium-temperature zone and the gas yield efficiency at 52° C. in the high-temperature zone. The capacity load of the vinasse at a fermentation temperature in the transition zone may reach 7.5 KgCOD/m³ d, the COD removal rate may reach 85% or above, and a capacity gas yield may reach 4 m³/m³ d.

Example 3

The slurry of the present invention was hydrolyzed cow manure slurry that stayed for at least 24 hours, and a TS concentration ranged from 8% to 10% by mass percentage. As shown in FIG. 6, before cow manure entered into the anaerobic tank 2, the cow manure was fed into a hydrolysis tank 10 to be subjected to stirred hydrolysis treatment at 35° C. to 40° C., stayed for at least 24 hours, then, was pumped into the front heat exchanger 1 for increasing the temperature of the cow manure slurry to 45±0.2° C., and then, was delivered to the anaerobic tank 2.

In an initial state, the central agitator 5 was turned on after feeding was completed, to slowly gently stir the slurry in the anaerobic tank 2 at 13.5 r/min to 14.5 r/min, where the stirring time may be 2±0.2 h. The central agitator 5 was turned off, to uniformly mix upper-layer, middle-layer, and lower-layer slurry in the anaerobic tank 2, to make the slurry come into full contact with the anaerobic sludge. A concentration of anaerobic sludge in the anaerobic tank 2 in the initial state was 8 to 12 g/l.

During operation, the pH value of the slurry in the anaerobic tank 2 ranged from 6.8 to 7.5, the concentration of the sludge ranged from 20 to 25 g/l, the TS concentration of the slurry ranged from 5% to 6%, and the fermentation temperature of the slurry was controlled at 43° C., 44° C., and 45° C. respectively for anaerobic reaction. After the fermentation temperature of the slurry in the anaerobic tank 2 increased due to environmental factors, when it was detected that a temperature difference between any two measurement points at a same layer was greater than 2° C. or a temperature difference between any two layers was greater than 2° C., the automatic control system automatically turned on the warming device, the central agitator 5, and the biogas slurry reflux pump 3. A reflux ratio of the biogas slurry and the slurry ranged from 2:1 to 6:1, to make the fresh material come into full and uniform contact with the anaerobic sludge. When it was detected that a temperature difference between any two measurement points at a same layer was less than PC or a temperature difference between any two layers was less than PC, the automatic control system controls the warming device and the biogas slurry reflux pump 3 to stop working and the central agitator 5 lag to stop working. The temperature in the tank was controlled within a specified range, and organic substances in the cow manure slurry were continuously treated and converted into methane, carbon dioxide, and water. The biogas was collected through an exhaust pipe. The effluent after sludge-water separation was collected for post-treatment, and discharged or partially reused after meeting standards.

Figure 7:
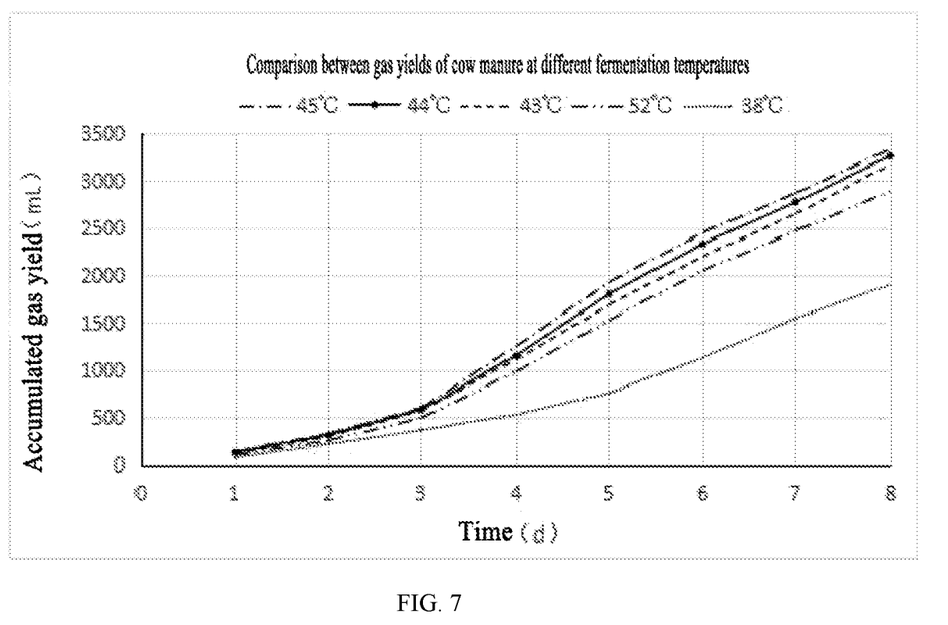
FIG. 7 is a schematic curve graph of comparison between gas yields of cow manure slurry at different fermentation temperatures according to the present invention.

FIG. 7 showed comparison between gas yields at different corresponding temperatures according to the present invention, where the fermentation temperatures of the slurry were 38° C., 43° C., 44° C., 45° C., and 52° C. It can be seen from FIG. 7 that in the present invention, the fermentation temperature of the cow manure slurry was controlled at 43° C., 44° C., and 45° C. Upon comparison between gas yields at 43° C., 44° C., and 45° C. and gas yields at a medium temperature and a high temperature, the gas yield efficiency of the cow manure at 44° C. in the transition zone was higher than the gas yield efficiency at 38° C. in the medium-temperature zone by 76.7% and was higher than the gas yield efficiency at 52° C. in the high-temperature zone by 12.9%. The gas yield efficiency at 43° C. and 45° C. in the transition zone was also higher than the gas yield efficiency at 38° C. in the medium-temperature zone and the gas yield efficiency at 52° C. in the high-temperature zone.

Example 4

The slurry of the present invention was hydrolyzed stalk slurry that stayed for at least 48 hours. The stalks may be corn stalks, dry wheat stalks, dry straws and weeds, and the like. As shown in FIG. 8, after being chopped, corn stalks were subjected to silage dipping in a silage pit 11, and then, were fed into a hydrolysis tank 10 to be subjected to stirred hydrolysis treatment at 35° C. to 40° C., stayed for 2 to 3 days. The stalk slurry in the hydrolysis tank 10 was pumped into the front heat exchanger 1 for increasing the temperature of the stalk slurry to 45±0.2° C., and then, was delivered to the anaerobic tank 2.

In an initial state, the central agitator 5 was turned on after feeding was completed, to slowly gently stir the slurry in the anaerobic tank 2 at 14 r/min, where the stirring time may be 2±0.2 h. The central agitator 5 was turned off, to uniformly mix upper-layer, middle-layer, and lower-layer slurry in the anaerobic tank 2, to make the slurry come into full contact with the anaerobic sludge. A concentration of anaerobic sludge in the anaerobic tank in the initial state was 8 g/l.

During operation, the pH value of the slurry in the anaerobic tank was 7, the concentration of the sludge was 22 g/l, the TS concentration of the slurry ranged from 5% to 6%, and the fermentation temperature of the slurry was controlled at 43° C., 44° C., and 45° C. respectively for anaerobic reaction. For specific temperature control, reference may be made to Example 3. Organic substances in the stalk slurry were continuously treated and converted into methane, carbon dioxide, and water at specified fermentation temperatures. The biogas was collected through an exhaust pipe. The effluent after sludge-water separation was collected for post-treatment, and discharged or partially reused after meeting standards.

Figure 9:
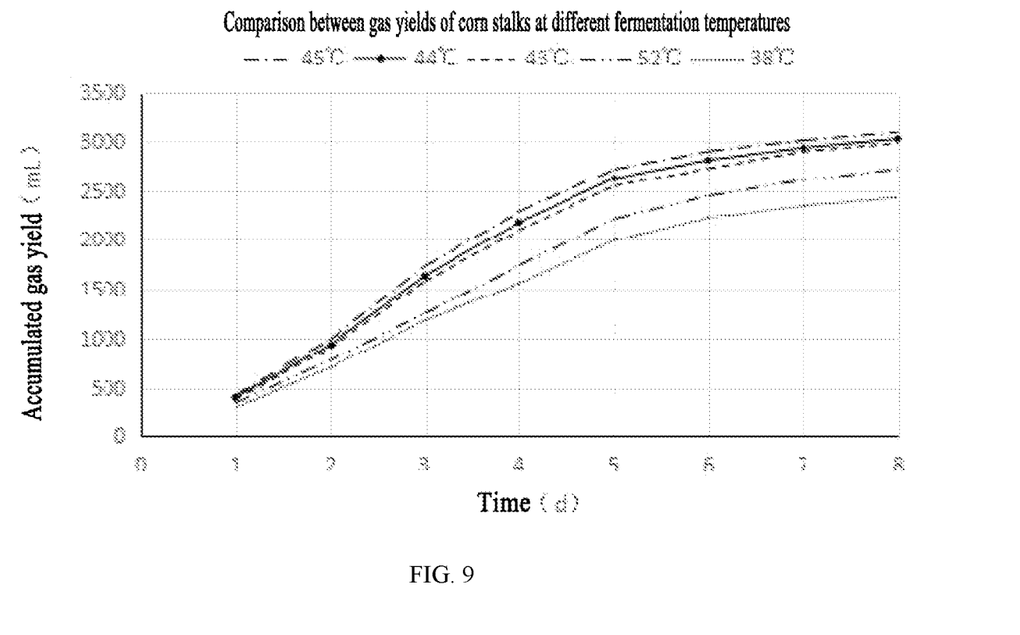
FIG. 9 is a schematic curve graph of comparison between gas yields of stalk slurry at different fermentation temperatures according to the present invention.

FIG. 9 showed comparison between gas yields at different corresponding temperatures according to the present invention, where the fermentation temperatures of the slurry were 38° C., 43° C., 44° C., 45° C., and 52° C. It can be seen from FIG. 9 that in the present invention, the fermentation temperature of the corn stalk slurry was controlled at 43° C., 44° C., and 45° C. Upon comparison between gas yields at 43° C., 44° C., and 45° C. and gas yields at a medium temperature and a high temperature, the gas yield efficiency of the corn stalk slurry at 44° C. in the transition zone was higher than the gas yield efficiency at 38° C. in the medium-temperature zone by 24.6% and was higher than the gas yield efficiency at 52° C. in the high-temperature zone by 11.1%. The gas yield efficiency at 43° C. and 45° C. in the transition zone was also higher than the gas yield efficiency at 38° C. in the medium-temperature zone and the gas yield efficiency at 52° C. in the high-temperature zone.

What is claimed is:

1. A method for improving efficiency of anaerobic fermentation in a medium temperature-high temperature transition zone, comprising the following steps:
   (1) performing a heat exchange on a hydrolyzed slurry through a front heat exchanger, and then pumping a resulting hydrolyzed slurry into a bottom of an anaerobic tank uniformly from a plurality of water distribution pipes at the bottom of the anaerobic tank, wherein a temperature of the resulting hydrolyzed slurry after the heat exchange performed through the front heat exchanger is 45±0.2° C., a thermal insulation layer and a warming device are arranged on a wall of the anaerobic tank, and an intermittently-operating central agitator with upper blades and lower blades is arranged inside the anaerobic tank, wherein a slurry before hydrolysis is one of a food waste slurry, a vinasse slurry, a cow manure slurry, and a stalk slurry, and wherein the hydrolyzed slurry comprises an anaerobic sludge comprising methanogenic bacteria;
   (2) in an initial state, turning on the intermittently-operating central agitator to stir the resulting hydrolyzed slurry in the anaerobic tank, wherein a rotational speed of the intermittently-operating central agitator ranges from 12 to 15 r/min, and turning off the intermittently-operating central agitator after uniformly mixing the hydrolyzed slurry, and wherein the anaerobic sludge is at a first concentration of 5 to 15 g/l; and then
   (3) in an operating state when a pH value of the resulting hydrolyzed slurry in the anaerobic tank ranges from 6.8 to 7.8, and the anaerobic sludge increases to a second concentration of 20 to 30 g/l, by controlling the warming device, a biogas slurry pump, and the intermittently-operating central agitator of the anaerobic tank through an automatic control system, to control the fermentation temperature of the resulting hydrolyzed slurry at 44±1° C., and be fully mixed, to continuously treat and convert organic substances in the resulting hydrolyzed slurry when the resulting hydrolyzed slurry is under an anaerobic fermentation condition at 44±1° C.;
   wherein temperature sensors for monitoring temperatures of the resulting hydrolyzed slurry within the anaerobic tank perform a multi-point temperature measurement where the sensors are distributed with at least two sensors on each of the upper, middle, and lower parts of the anaerobic tank; when the temperature sensors detect a temperature difference between two measurement points at a same part of the upper, middle and lower parts of the anaerobic tank is greater than 2° C. or a temperature difference between two parts of the upper, middle and lower parts of the anaerobic tank is greater than 2° C., the automatic control system automatically turns on the warming device, the intermittently-operating central agitator, and the biogas slurry pump, to heat the slurry through the warming device and to pump a first upper-part biogas slurry to a first lower-part biogas slurry, wherein the first upper-part biogas slurry corresponds to the upper part of the anaerobic tank, wherein the first lower-part biogas slurry corresponds to the lower part of the anaerobic tank, and the intermittently-operating central agitator stirs the resulting hydrolyzed slurry; wherein the rotational speed of the intermittently-operating central agitator ranges from 12 to 15 r/min; and when the temperature sensors detect the temperature difference between the two measurement points at the same part of the first-upper-part biogas slurry and the first lower-part biogas slurry is less than 1° C. or the temperature difference between the two parts is less than 1° C., the automatic control system controls the warming device and the biogas slurry pump to stop working and the intermittently-operating central agitator lags to stop working.

2. The method for improving efficiency of anaerobic fermentation in the medium temperature-high temperature transition zone according to claim 1, wherein the hydrolyzed slurry is a food waste slurry after oil extraction and hydrolysis, a carbon-nitrogen ratio of the food waste slurry ranges from 13:1 to 15:1, and a TS concentration of the food waste slurry ranges fro 10% to 20% by a mass percentage; and when a COD of the food waste slurry ranges a from 120,000 to 180,000 mg/l, the automatic control system automatically turns on the intermittently-operating central agitator and the biogas slurry pump.

3. The method for improving efficiency of anaerobic fermentation in the medium temperature-high temperature transition zone according to claim 1, wherein the hydrolyzed slurry is a vinasse slurry after hydrolysis, a carbon-nitrogen ratio of the vinasse slurry ranges from 13:1 to 15:1, and a TS concentration of the vinasse slurry ranges from 6% to 8% by a a mass percentage; and when a COD of the vinasse slurry ranges from 60,000 to 80,000 mg/l automatic control system automatically turns on the intermittently-operating central agitator and the biogas slurry.

4. The method for improving efficiency of anaerobic fermentation in the medium temperature-high temperature transition zone according to claim 1, wherein the hydrolyzed slurry is a cow manure slurry after hydrolysis and staying for at least 24 hours, and a TS concentration of the cow manure slurry ranges from 8% to 10% by a mass percentage.

5. The method for improving efficiency of anaerobic fermentation in the medium temperature-high temperature transition zone according to claim 1, wherein the hydrolyzed slurry is a stalk slurry after hydrolysis and staying for at least 2 to 3 days.

* * * * *